United States Patent [19]

Rusek

[11] Patent Number: 4,921,980
[45] Date of Patent: May 1, 1990

[54] PROCESS FOR THE PREPARATION OF N-ALKYLANILINES

[75] Inventor: Milos Rusek, Binningen, Switzerland

[73] Assignee: Ciba-Geigy Corporation, Ardsley, N.Y.

[21] Appl. No.: 53,245

[22] Filed: May 22, 1987

Related U.S. Application Data

[63] Continuation-in-part of Ser. No. 822,971, Jan. 27, 1986, abandoned, which is a continuation-in-part of Ser. No. 696,235, Jan. 29, 1985, abandoned.

[51] Int. Cl.$^5$ .................. C07D 315/00; C07C 149/42
[52] U.S. Cl. .................................... 549/426; 549/492; 564/341; 564/392; 564/401
[58] Field of Search ...................... 564/341, 392, 401; 549/426, 492

[56] References Cited

U.S. PATENT DOCUMENTS 3,700,745 10/1972 Kouach et al. ...................... 502/242
3,764,562 10/1973 Kittrell et al. ...................... 502/242
4,183,868 1/1980 Radimerski et al. ................ 260/573
4,429,155 1/1984 Göetz et al. ......................... 564/402

OTHER PUBLICATIONS

Lecture by Mr. Rusek at 9th International Congress on Catalysis, 6/26–7/1/88.

Primary Examiner—Richard L. Raymond
Assistant Examiner—Raymond Covington
Attorney, Agent, or Firm—Kevin T. Mansfield

[57] ABSTRACT

A process for the preparation of N-alkylanilines is described, the most essential feature of which comprises reacting corresponding anilines at 150° to 300°C. with corresponding alcohols in the presence of a catalyst consisting of silica gel as carrier, of 0.2 to 10% of platinum and of 0.05 to 3% of a compound of a metal of the groups Ia and/or IIa of the Periodic Table, with the catalyst additionally containing at least one compound of an element of the groups Ib, IVa, IVb, Vb, VIIb and VIII in such an amount that the atomic ratio of platinum to the sum of these elements is 1 to 6.

16 Claims, No Drawings

PROCESS FOR THE PREPARATION OF N-ALKYLANILINES

This is a continuation-in-part of my application, Ser. No. 822,971, filed Jan. 27, 1986, now abandoned, which in turn is a continuation-in-part of my application Ser. No. 696,235, filed Jan. 29, 1965, now abandoned.

The present invention relates to a process for the preparation of N-alkylanilines of the formula I

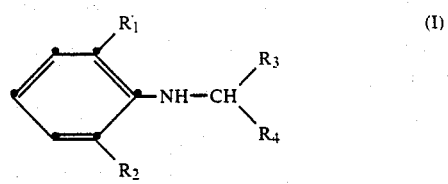

wherein
$R_1$ and $R_2$ are each independently halogen $C_1$–$C_6$alkyl, $C_1$–$C_6$alkoxy or hydrogen
$R_3$ is $C_1$–$C_6$alkyl, $C_3$–$C_6$cycloalkyl, $C_1$–$C_4$alkoxy, $C_1$–$C_4$alkoxy-$C_1$–$C_4$alkyl, phenyl, or hydrogen,
$R_4$ is $C_1$–$C_6$alkyl, $C_1$–$C_4$alkoxy, furfuryl, tetrahydrofurfuryl or hydrogen, and $R_3$ and $R_4$ together with the carbon atom to which they are attached can form a 4- to 7-membered isocyclic ring which is unsubstituted or substituted by one or two $C_1$–$C_4$alkyl groups or pyran or a tetrahydropyran ring, and to a catalyst for carrying out said process.

In above formula and in the text given hereinafter halogen denotes fluorine, chlorine and bromine; preferably fluorine and chlorine. $C_1$–$C_6$alkyl is methyl, ethyl, n-propyl, iso-propyl, n-butyl, sek-butyl, iso-butyl, tert-butyl and the isomeric pentyl and hexyl radicals.

$C_3$–$C_6$cycloalkyl is cyclopropyl, cyclobutyl, cyclopentyl and cyclohexyl.

$C_1$–$C_4$alkoxy-$C_1$–$C_4$-alkyl denotes the combinations of $C_1$–$C_4$alkyl-oxy-groups bound through the oxygen atom to another $C_1$–$C_4$-alkyl moiety forming for example a methoxymethyl, n-propyloxymethyl, ethoxymethyl, methoxyethyl, 2-methoxy-1-methyl-ethyl or a 2-ethoxy-1-methyl-ethyl substituent.

N-alkylanilines of the formula I are valuable intermediates for the preparation of pesticidal active compounds. Thus, N-alkylanilines of the formula I can be converted by means of haloacetyl halides, such as chloroacetyl chloride or bromoacetyl bromide, into the corresponding acetanilides having a pesticidal action. Acetanilides of this type and their preparation and use are described, for example, in U.S. Pat. Nos. 2,863,752, 3,345,151, 3,268,584, 3,952,056 and 3,937,730, in French Pat. No. 1,339,001 und in German Pat. No. 2,305,495 and German Auslegeschrift 2,328,340.

It is known to prepare N-alkylanilines by reacting anilines with alkyl halides, alkyl tosylates or alkyl phosphates. When this method is used, however, considerable amounts of N,N-dialkylanilines are always formed in addition to the desired N-monoalkylanilines. Therefore, because its selectivity is too low, this process is unsuitable for industrial preparation of compounds of the formula I. Moreover, this process presents ecological problems since the waste waters always contain large amounts of hydrogen halide, toluenesulfonic acid or phosphoric acid, or salts of these acids.

It has also already been proposed to react anilines in the presence of catalysts with alcohols to give N-alkylanilines (cf. Kirk-Othmer, Encyclopaedia of Chemical Technology, 2nd edition, volume 2, 412-13). Catalysts used in this process were, in addition to aluminium oxide, aluminium silicate, a mixture of phosphoric acid and bentonite, and mineral acids, such as hydrochloric acid or sulfuric acid, also hydrogen transfer catalysts. For example, according to a process described in U.S. Pat. No. 2,580,284, aniline is reacted, in the presence of a copper-containing alumina catalyst and in the presence of hydrogen, with methanol to give N-methylaniline in a yield of 96% of theory. Furthermore, ethanol can be reacted in the presence of Raney nickel to give N-ethylaniline in a yield of 80 to 83% of theory (cf. J. Org. Chem. 21, 474-(1956) and J. Amer. Chem. Soc. 77, 4052-54 (1955)). When aniline and methanol are reacted in the presence of copper chromite and hydrogen, N-methylaniline is formed in virtually quantitative yield as the sole reaction (cf. Japanese Published Specification No. 73/49,727; C.A. 79, (1973) 136.769w and German Published Specification No. 2,061,709).

As the above discussion of the state of the art shows, the reaction of anilines which are unsubstituted at the ortho-position of the benzene ring with alcohols in the presence of hydrogen and hydrogen transfer catalysts results in N-alkylanilines in excellent yield. However, it is not possible to obtain a good yield by these processes by reacting o-mono- or o,o-disubstituted anilines with alcohols, and especially with alkoxyalkanols, to give the corresponding N-alkylanilines.

In accordance with U.S. Pat No. 4,138,868, the monoalkylation of 2,6-dialkylanilines with alcohols can be carried out in the presence of a copper-containing catalyst containing a small amount of palladium or platinum in the temperature range from 200° to 350° C. With primary alcohols this alkylation results in a moderate to good yield, whereas with secondary alcohols conversion, selectivity and yield are unsatisfactory.

The drawbacks of the prior art catalysts have been discussed during a lecture held at June 3, 1986 at the "1st International Symposium on Organic Chemistry in Technological Perspective" at Jerusalem, Israel. A palladized Copper oxide/Chromium oxide catalyst (Pd-CuCr-oxide, as described in U.S. No. 4,183,868) has been investigated as N-alkylating catalyst using the conversion of sterically hindered anilines (II) with primary and secondary methoxy-alcoholes (III') as model reaction

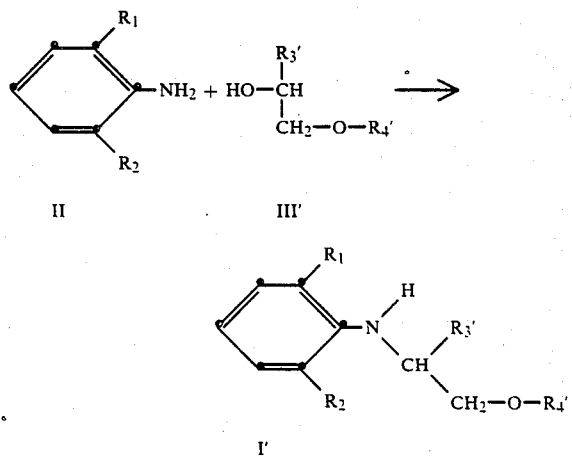

The conversion rate and selectivity found at 225° C. and 1 bar H₂ is as given below:

|     | R₁  | R₂    | R₃'  | R₄' | Conversion (%) | Selectivity (%) |
|-----|-----|-------|------|-----|----------------|-----------------|
| (a) | CH₃ | CH₃   | H    | CH₃ | 81             | 96              |
| (b) | CH₃ | C₂H₅  | H    | CH₃ | 56             | 94              |
| (c) | CH₃ | CH₃   | CH₃  | CH₃ | 22             | 11              |
| (d) | CH₃ | C₂H₅  | CH₃  | CH₃ | 23             | 8               |

The use of Pt-SiO₂, of calcinated Pt-SiO₂ or of a Pt-SiO₂-catalyst promoted with Sn did not improve the conversion rate and the selectivity of above reaction as it has been discussed in case of examples (e), (f) and (g) (reaction conditions: 200° C. and 1 bar H₂); concerning the reaction of 2-ethyl-6-methylaniline with 3-methoxypropan-2-ole to the N-substituted aniline I' (R₁, R₃' and R₄'=CH₃, R₂=C₂H₅).

| Catalyst-system | R₁ | R₂ | R₃' | R₄' | Conversion (%) | Selectivity (%) |
|---|---|---|---|---|---|---|
| (e) Pt-SiO₂ | CH₃ | C₂H₅ | CH₃ | CH₃ | 2 | 29 |
| (f) Pt-SiO₂ (Ca²⁺) | CH₃ | C₂H₅ | CH₃ | CH₃ | 3 | 65 |
| (g) Pt, Sn—SiO₂ | CH₃ | C₂H₅ | CH₃· | CH₃ | 14 | 93 |

Accordingly, the object of the present invention is to provide a process by which anilines and their o-mono- or o,o-disubstituted derivatives can be reacted with primary and secondary alcohols to give the corresponding N-alkylanilines in good yields.

It has now been found that N-alkylanilines of the formula I

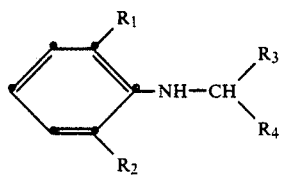
(I)

wherein R₁ and R₂ are defined for formula I, can be prepared in excellent yield by reacting an aniline of the formula II

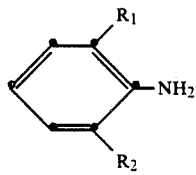
(II)

wherein R₁ and R₂ are defined for formula I, with an alcohol of the formula III

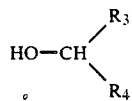
(III)

wherein R₃ and R₄ are as defined for formula I, in the presence of hydrogen and a catalyst, which reaction is carried out in the temperature range from 150° to 300° C. and under a pressure of 0,5 to 6 bar, in the presence of a catalyst consisting of silica gel as carrier and 0.2 to 10% of platinum and 0.05 to 3% of a compound of a metal of the groups Ia and/or IIa of the Periodic Table, said catalyst additionally containing at least one compound of an element of the groups Ib, IVa, Vb, VIIb and VIII in an amount such that the atomic ratio of platinum to the sum of these elements is 1 to 6.

The notification of the elements used in this application is taken in accordance with the CAS-system.

Group IA and IIA elements are Li, Na, K, Rb, Cs, Be, Mg, Ca, Sr and Ba.
Group IVb is Ti, Zr and Hf
Group Vb is V, Nb and Ta
Group VIIb is Mn, Tc and Re
Group VIII is Fe, Co, Ni, Ru, Rh, Pd, Os, Ir and Pt
Group Ib is Cu, Ag and An and
Group IVa is Ge, Sn and Pb.

Silica, which can formally be considered as well as Carbon as a member of Group IVa is not included within this definition. But silica forms a part of the silica gel carrier.

In particular, the present invention relates to a process for the preparation of N-alkylanilines of the formula I, wherein R₁ is C₁-C₃alkyl or hydrogen, R₂ is C₁-C₃alkyl or C₁-C₂alkoxy, R₃ is C₁-C₃alkoxymethyl, R₄ is methyl or hydrogen, and wherein R₃ and R₄ together with the carbon atom to which they are attached form a cycloalkyl, 2-methylcyclohexyl or 2,6-dimethylcyclohexyl radical.

The present invention also relates in particular to a process for the preparation of N-alkylanilines of the formula I, wherein R₄ is C₁-C₆alkyl, C₁-C₄-alkoxy, furfuryl or tetrahydrofurfuryl.

The present invention relates further in particular to a process for the preparation of N-alkylanilines of the formula I, wherein R₃ and R₄ together with the carbon atom to which they are attached form a pyran or a tetrahydropyran ring.

Most particularly, the present invention relates to a process for the preparation of 2-methyl-6-ethyl-N-(1-methyl-2-methoxyethyl)aniline and 2,6-diethyl-N-2-propoxyethylaniline.

The preferred temperature range for the process of the present invention is normally from 175° to 225° C., the preferred pressure range is from 1 to 4 bar.

The hourly rate of addition of aniline of the formula II is conveniently 0.5 to 10 moles, preferably 1 to 5 moles, per liter of catalyst.

The molar ratio of the alcohol of the formula III to the aniline of the formula II is normally 0.1 to 10, preferably 1.1 to 2.1.

The addition of hydrogen is conveniently 0.5 to 10 moles, preferably 0.8 to 1.2 moles, per mole of the aniline of the formula II employed.

Suitable carriers for the catalysts of the present invention are silica gels with the following properties:

| specific surface area | 300–700 m²/g |
|---|---|
| pore volume | 0.25–1.0 ml/g |
| average pore radius | 1–8 nm |
| bulk density | 0.25–0.9 g/ml |
| water content | 1–5% |
| iron, aluminium and titanium content, total max. | 750 ppm |

The silica gels employed may be commercially available products providing they meet the requirements of this specification. Further, commercially available products with too high an iron, aluminium and titanium content can be converted into carriers suitable for the present invention by washing out with dilute acids, e.g. 10% aqueous hydrochloric acid. In the products resulting in this reaction the total content of iron, aluminium and titanium should be below 750 ppm, preferably below 500 ppm, with the content of each one of the metals indicated preferably being below 200 ppm.

Particularly suitable is a silica gel with the following properties:

| | |
|---|---|
| specific surface area | 400–600 m$^2$/g |
| pore volume | 0.35–0.75 ml/g |
| average pore radius | 2–4 nm |
| bulk density | 0.65–0.75 g/ml |
| water content | 1.5–2.5% |
| iron, aluminium and titanium content, max. | 500 ppm |

The silica gel employed as carrier is stabilised, after an optional washing with dilute acid, by keeping it at a temperature above 500° C. for several hours.

To prepare the catalyst, a suitable platinium compound, e.g. hexachloroplatinic acid, and at least one water-soluble compound of the elements of groups Ib, IVa, IVb, Vb, VIIb and VIII of the Periodic Table, as promoter, is applied in solution to the precalcined silica gel as carrier such that the solution is absorbed by the carrier (impregnation). In most cases a suitable solvent is water.

Products which are unstable in water, e.g. germanium tetrachloride, are dissolved in an inert organic solvent, e.g. methylene chloride. After application of these products, the resultant mixture is dried in vacuo at 80° to 150° C., whereupon at least one compound of the elements of groups Ia and IIa of the Periodic Table, as second promoter, is applied in the same manner. Suitable compounds are e.g. the hydroxides or chlorides. The application of the two promoter types can also be made in reverse order.

The catalyst is subsequently dried again and then calcined by keeping it in the temperature range of 400° C. for several hours. The crude catalyst so obtained is put, after cooling, into the reactor and activated at the beginning of an experiment.

The catalyst of the present invention is novel and likewise constitutes an object of the invention.

The activation of the crude catalyst is effected in the reactor in a stream of gas under atmospheric pressure for several hours at 140° C., during which activation the composition of the gas is gradually changed from nitrogen to hydrogen. The ultimately obtained catalyst consists of silica gel, platinium and of at least one compound of the elements of groups Ib, IVa, IVb, Vb, VIIb and VIII of the Periodic Table and of at least one compound of the elements of groups Ia and IIa of the Periodic Table and can be employed in the process of the present invention.

Among the novel catalysts in the presence of which the process of the present invention for the preparation of compounds of the formula I can be carried out, the following compositions are preferred:

(a) 0.5–6% of platinum, 0.1–2% of at least one compound selected from the elements consisting of lithium, sodium, potassium, rubidium, cesium, beryllium, magnesium, calcium, strontium or barium, at least one compound selected from the elements consisting of copper, germanium, tin, lead, titanium, niobium, manganese and ruthenium, with the atomic ratio of platinum to the sum of these elements being 2.5 to 3.5.

(b) 0.5–6% of platinum, 0.1–2% of at least one compound selected from the elements consisting of lithium, sodium, potassium, rubidium, cesium, beryllium, magnesium, calcium, strontium or barium, a rhenium compound, with the atomic ratio of platinum to rhenium being 0.5 to 1.5.

Among the novel catalysts, the following composition is most preferred:

3–5% of platinum, 0.1–2% of a calcium compound, a tin(II) compound in the atomic ratio of platinum:tin = 2.5 to 3.5.

A catalyst which has been deactivated after prolonged operation can be reactivated, after a regeneration of several hours at 450° to 600° C. in a stream of air, by a method of activation analogous to the one described above, and reused.

The process of the present invention is conveniently carried out continuously in a fixed-bed reactor or a trickle-bed apparatus. The mixture flowing through the reactor can either be in pure gaseous form or can form a gas and liquid phase.

The two educts can either be introduced separately into the reactor or as a mixture prepared in the desired ratio. It is advantageous to add the educts in fluid state, to which end they must, if necessary, be heated. Depending on the reaction conditions, the educts may, before entry into the reactor, be further heated and also evaporated.

The resultant reaction mixture can be analysed by gas chromatography. The preparative separation thereof can be effected by conventional methods of separation. The hydrogen and the unreacted educts can be reused when carrying out the process industrially.

By the process of the present invention, aniline and its o-mono- and o,o-disubstituted derivatives can be alkylated with alcohols in very good yield. Moreover, the process of the present invention also makes it possible to carry out the alkylation with secondary alcohols in equally good yield. As a result, the intermediates of the formula I with high conversion and excellent selectivity can be prepared using inexpensive, readily accessible alcohols. Because of the short reaction times, the process can easily be carried out continuously and is therefore very suitable for an industrial preparation of intermediates of the formula I. The activity of the catalyst decreases markedly only after about one day of continuous operation. Continuous operation of the reaction can be maintained by cyclic repetition of the operational steps comprising activation, reaction, regeneration, then reactivation, reaction etc. When carrying out the reaction on an industrial scale, uniform continuous production can be ensured by two or more parallel reactors with appropriately displaced operational steps.

Compared with those processes in which the alkylation is carried out with alkyl halides or alkyl tosylates, the process also offers substantial advantages from an ecological point of view, since the high-loading of the waste water with salts, which arises in the case of the former processes, does not occur.

The process of the present invention is illustrated in more detail by the following Examples:

EXAMPLE 1

Preparation of
2-methyl-6-ethyl-N-(1-methyl-2-methoxethyl)aniline 9.5 g of an average pore size silica gel having the following characteristics:

| | |
|---|---|
| surface area (BET) | 468 m²/g |
| pore volume | 0.62 ml/g |
| average pore radius | 2.65 nm |
| content of calcium | <10 ppm |
| magnesium | <10 ppm |
| iron | 115 ppm |
| potassium | <20 ppm |
| sodium | <50 ppm |
| aluminium | 155 ppm |
| titanium | 180 ppm | are impregnated with 7.5 ml of an aqueous solution consisting of 2.5 g of hexachloroplatinic acid.xH$_2$O (5.1 mmol) and 0.38 g of tin(II) chloride.2H$_2$O (1.7 mmol), thoroughly mixed and dried for 2 hours at 90° C. in vacuo. The resultant mixture is additionally impregnated with 6 ml of an aqueous solution consisting of 0.37 g of calcium chloride-dihydrate (2.5 mmol) and mixed. After renewed drying at 90° C. in vacuo, the mixture is calcined by keeping it at 350° C. for 5 hours, thus affording 15 ml of the catalyst to be activated.

4.6 ml of this crude catalyst are activated in a microreactor with a 50 ml/min stream of hydrogen/nitrogen gas at 140° C. for 1½ hours, while increasing the hydrogen content linearly from 0 to 100% during the first hour. Subsequently, the stream of hydrogen is adjusted to 3.75 ml/min (9.2 mmol/h) and the temperature in the reactor is raised to 200° C. Then at a rate of 3 ml/h a mixture of 135.2 g (1 mol) of 2-methyl-6-ethylaniline and 180.2 g (2 mol) of 1-methoxypropanol-2 is pumped into the reactor, evaporated and passed in gaseous form over the layer of catalyst, which corresponds to a rate of addition of 2 mol of 2-methyl-6-ethylaniline per hour and per liter of catalyst. For a reaction time of 15 hours the following results are obtained: total conversion, based on 2-methyl-6-ethylaniline, ($C_A$): 65.4% selectivity, based on 2-methyl-6-ethylaniline, ($S_A$): 93,7%

The addition of hydrogen and educt is then replaced by a 50 ml/min stream of nitrogen/air, while increasing the proportion of air linearly from 0 to 100% and the temperature from 190° to 450° C. over 1½ hours. The catalyst is kept under these conditions for 3 hours and then cooled in a stream of nitrogen to 140° C. and, as described above, activated with hydrogen.

Subsequently, the above-described cycle is commenced, the duration of which is 24 hours. The activity of the catalyst increases after the first cycles compared with the first passage.

Only after several weeks' operation do the results show a marked decrease in selectivity.

In accordance with the process of the present invention, further Examples are carried out with the same catalyst. The results are given in the following Table:

TABLE

| No. | R$_1$ | R$_2$ | R$_3$ | R$_4$ | rate of addition moles of aniline (II) per liter of catalyst · h | temp. °C. | conversion $C_A$* | selectivity $S_A$* |
|---|---|---|---|---|---|---|---|---|
| 1 | CH$_3$— | C$_2$H$_5$— | —CH$_2$OCH$_3$ | CH$_3$— | 2 | 200 | 65,4 | 93,7 |
| 2 | H— | CH$_3$— | —CH$_2$OCH$_3$ | H— | 6 | 190 | 75,5 | 94,2 |
| 3 | H— | CH$_3$— | —CH$_2$—OCH$_3$ | CH$_3$— | 4 | 200 | 94,3 | 98,7 |
| 4 | H— | C$_2$H$_5$— | —CH$_2$—OCH$_3$ | CH$_3$— | 4 | 200 | 92,1 | 98,6 |
| 5 | H— | OCH$_3$— | —CH$_2$OCH$_3$ | H— | 1 | 175 | 92,7 | 91,7 |
| 6 | H— | OCH$_3$— | —CH$_3$OCH$_3$ | CH$_3$— | 1 | 225 | 79,5 | 94,7 |
| 7 | H— | OC$_2$H$_5$— | —CH$_2$OCH$_3$ | CH$_3$ | 2 | 200 | 97,5 | 97,0 |
| 8 | CH$_3$— | CH$_3$— | —CH$_2$OCH$_3$ | H— | 4 | 190 | 38,1 | 94,9 |
| 9 | CH$_3$— | CH$_3$— | —CH$_2$OCH$_3$ | CH$_3$— | 4 | 200 | 56,2 | 95,6 |
| 10 | C$_2$H$_5$— | C$_2$H$_5$— | —CH$_2$O-nC$_3$H$_7$ | H— | 4 | 190 | 52,1 | 89,7 |
| 11 | CH$_3$— | CH$_3$— | —CH$_2$O-nC$_3$H$_7$ | H— | 4 | 190 | 52,1 | 89,7 |
| 12 | CH$_3$— | C$_2$H$_5$— | —CH$_2$OCH$_3$ | H— | 4 | 190 | 62,0 | 91,1 |
| 13 | C$_2$H$_5$— | C$_2$H$_5$— | —CH$_2$OCH$_3$ | CH$_3$— | 4 | 200 | 52,3 | 89,0 |
| 14 | i-C$_3$H$_5$— | i-C$_3$H$_7$— | —CH$_2$OCH$_3$ | CH$_3$— | 2 | 200 | 36,2 | 79,1 |
| 15 | i-C$_3$H$_7$— | i-C$_3$H$_7$— | —CH$_2$OCH$_3$ | CH$_3$— | 2 | 200 | 53,7 | 86,0*** |
| 16 | CH$_3$— | CH$_3$— | —CH$_2$—(CH$_2$)$_3$—CH$_2$— | | 2 | 200 | 71,7 | 91,2** |
| 17 | CH$_3$— | H— | —CH(2-CH$_3$)(CH$_2$)$_3$—CH$_2$— | | 2 | 200 | 65,4 | 95,4 |
| 18 | CH$_3$— | H— | —CH(2-CH$_3$)—(CH$_2$)—CH(6-CH$_3$)— | | 2 | 200 | 60,9 | 94,0 |
| 19 | H— | H— | —CH$_2$OCH$_3$ | H— | 6 | 190 | 51,1 | 95,8 |
| 20 | H— | H— | —CH$_2$OCH$_3$ | CH$_3$— | 8 | 225 | 66,9 | 97,8 |
| 21 | CH$_3$— | CH$_3$— | —H | —CH$_2$—CH(—CH$_2$—CH$_2$—O—CH$_2$—CH$_2$—) | | 190 | 68,3 | 90,2**** |
| 22 | CH$_3$— | CH$_3$— | —H | —CH$_2$—C(=CH—CH=CH—O—) | 2 | 200 | 67,5 | 91,3***** |
| 23 | CH$_3$— | CH$_3$— | —(CH$_2$)$_2$—O—(CH$_2$)$_2$— | | 2 | 200 | 65,7 | 89,2**** |
| 24 | CH$_3$— | H— | —CH(3-CH$_3$)—CH$_2$—O—(CH$_2$)$_2$— | | 2 | 200 | 60,4 | 91,2**** |
| 25 | Cl | Cl | —CH$_2$—O—CH$_3$ | CH$_3$ | 2 | 200 | 37,3 | 82,3 |

TABLE-continued

| No. | Educts and products of the formulae I + II | | | | rate of addition moles of aniline (II) per liter of catalyst · h | temp. °C. | conversion C₄* | selectivity S₄* |
|---|---|---|---|---|---|---|---|---|
| | R₁ | R₂ | R₃ | R₄ | | | | |
| 26 | F | F | —CH₂—O—CH₃ | CH₃ | 2 | 200 | 41.5 | 85.6 |

*s. Example 1
**R₃ and R₄ together. according to definition (page 1)
***For the preparation of the catalyst (according to Example 1) calcium chloride was replaced by 2.5 mmol of barium chloride
****Sum of desired and dehydrogenated products
*****Sum of desired and hydrogenated products

What is claimed is:

1. A process for the preparation of an N-alkyl-aniline of the formula I

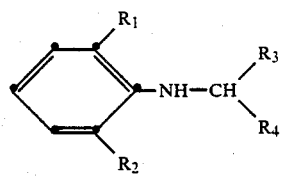

wherein
R₁ and R₂ are each independently halogen, C₁-C₆alkyl, C₁-C₆alkoxy or hydrogen,
R₃ is C₁-C₆alkyl, C₃-C₆cycloalkyl, C₁-C₄alkoxy, C₁-C₄alkoxy-C₁-C₄alkyl, phenyl or hydrogen,
R₄ is C₁-C₆alkyl, C₁-C₄alkoxy, furfuryl, tetrahydrofurfuryl or hydrogen, and R₃ and R₄ together with the carbon atom to which they are attached can form a 4- to 7-membered isocyclic ring which is unsubstituted or substituted by one or two C₁-C₄alkyl groups or a pyran or a tetrahydropyran ring, with the proviso that at least one of R₁ or R₂ is hydrogen when R₃ and R₄ form a 4 to 7 membered isocyclic ring which ring is disubstituted in the α- and α'-position by a C₁-C₄alkyl group by reacting an aniline of the formula II

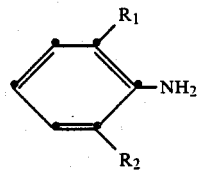

wherein R₁ and R₂ are as defined for formula I, with an alcohol of the formula III

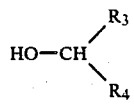

wherein R₃ and R₄ are as defined for formula I, in the presence of hydrogen and a catalyst, which process comprises carrying out the reaction in the temperature range from 150° to 300° C. and under a pressure of 0,5 to 6 bar, in the presence of a catalyst consisting of silica gel as carrier and 0.2 to 10% of platinum and 0.05 to 3% of a compound of a metal of the groups Ia and/or IIa of the Periodic Table, and catalyst additionally containing at least one compound of an element of the groups IVa, IVb, Vb and VIIb in an amount such that the atomic ratio of platinium to the sum of these elements is 1 to 6.

2. A process according to claim 1, which comprises carrying out the reaction in the temperature range from 175° to 225° C.

3. A process according to claim 1, which comprises carrying out the reaction under a pressure of 1 to 4 bar.

4. A process according to claim 1, which comprises carrying out the reaction with an hourly rate of addition of 0.5 to 10 moles of aniline of the formula II per liter of catalyst.

5. A process according to claim 4, which comprises carrying out the reaction with an hourly rate of addition of 1 to 5 moles of aniline of the formula II per liter of catalyst.

6. A process according to claim 1, wherein the molar ratio of the alcohol of the formula III to the aniline of the formula II is 0.1 to 10.

7. A process according to claim 6, wherein the molar ratio of the alcohol of the formula III to the aniline of the formula II is 1.1 to 2.1.

8. A process according to claim 1, wherein the addition of hydrogen is effected in the molar ratio of 0.5 to 10 moles per mole of aniline of the formula II.

9. A process according to claim 8, wherein the addition of hydrogen is effected in the molar ratio of 0.8 to 1.2 moles per mole of aniline of the formula II.

10. A process according to claim 1, wherein the catalyst consists of 0.5 to 6% of platinium, of 0.1 to 2% of at least one of the compounds selected from the elements consisting of lithium, sodium, potassium, rubidium, cesium, beryllium, magnesium, calcium, strontium or barium and of least one of the compounds selected from the elements consisting of germanium, tin, lead, titanium, niobium, rhenium and manganese, with the atomic ratio of platinum to the sum of these elements being 2.5 to 3.5.

11. A process for the preparation of an N-alkylaniline of the formula I

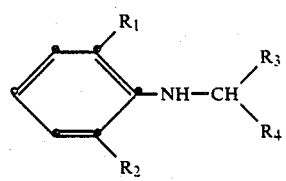

wherein
R₁ and R₂ are each independently halogen C₁-C₆alkyl, C₁-C₆alkoxy or hydrogen
R₃ is C₁-C₆alkyl, C₃-C₆cycloalkyl, C₁-C₄alkoxy, C₁-C₄alkoxy-C₁-C₄alkyl, phenyl or hydrogen
R₄ is C₁-C₆alkyl, C₁-C₄alkoxy, furfuryl, tetrahydrofurfuryl or hydrogen, and R₃ and R₄ together with the carbon atom to which they are attached can form a 4- to 7-membered isocyclic ring which is unsubstituted or substituted by one or two $C_1$-$C_4$alkyl groups or a pyran or a tetrahydropyran ring, with the proviso that at least one of $R_1$ or $R_2$ is hydrogen when $R_3$ and $R_4$ form a 4 to 7 membered isocyclic ring which ring is disubstituted in the $\alpha$- and $\alpha'$-position by a $C_1$-$C_4$alkyl group
by reacting an aniline of the formula II

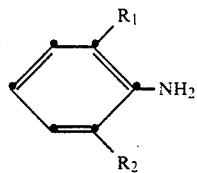  (II)

wherein $R_1$ and $R_2$ are as defined for formula I, with an alcohol of the formula III

  (III)

wherein $R_3$ and $R_4$ are as defined for formula I, in the presence of hydrogen and a catalyst, which process comprises carrying out the reaction in the temperature range from 150° to 300° C. and under a pressure of 0.5 to 6 bar, in the presence of a catalyst consisting of silica gel as carrier and 0.5 to 6% of platinum, of 0.1 to 2% of at least one compound of an element selected from the group consisting of lithium, potassium, rubidium, cesium, beryllium, magnesium, calcium, strontium or barium and of a rhenium compound, with the atomic ratio of platinum to rhenium being 0.5 to 1.5.

12. A process according to claim 1, wherein $R_1$ is $C_1$-$C_3$alkyl or hydrogen, $R_2$ is $C_1$-$C_3$alkyl or $C_1$-$C_2$alkoxy, $R_3$ is $C_1$-$C_3$alkoxymethyl, $R_4$ is methyl or hydrogen, and wherein $R_3$ and $R_4$ together with the carbon atom to which they are attached form a cyclohexyl, 2-methylcyclohexyl or 2,6-dimethylcyclohexyl radical.

13. A process according to claim 1, wherein $R_4$ is $C_1$-$C_6$-alkyl, $C_1$-$C_4$-alkoxy, furfuryl or tetrahydrofurfuryl.

14. A process according to claim 1, wherein $R_3$ and $R_4$ together with the carbon atom to which they are attached form a pyran or a tetrahydropyran ring.

15. A process according to claim 1, which comprises reacting 2-methyl-6-ethylaniline with 1-methoxypropanol-2 in the molar ratio of 1:1 to 2.1 with the addition of 1 mole of hydrogen per mole of 2-methyl-6-ethylaniline, in the presence of a catalyst consisting of 3 to 5% of platinum, of 0.1 to 2% of a calcium compound and of a tin(II) compound in the atomic ratio of platinum:tin=2.5 to 3.5, at 200° C. and under normal pressure to give 2-methyl-6-ethyl-N-(1-methyl-2-methoxyethyl)aniline.

16. A process according to claim 1, which comprises reacting 2,6-diethylaniline with 2-propoxyethanol in the molar ratio of 1:1 to 2.1 with the addition of 1 mole of hydrogen per mole of 2,6-diethylaniline, in the presence of a catalyst consisting of 3 to 5% of platinum, of 0.1 to 2% of a calcium compound and of a tin(II) compound in the atomic ratio of platinum:tin=2.5 to 3.5, at 190° C. and under normal pressure to give 2,6-diethyl-N-2-propoxyethylaniline.

* * * * *